(12) United States Patent
Barthold et al.

(10) Patent No.: US 8,641,749 B2
(45) Date of Patent: Feb. 4, 2014

(54) STENT DELIVERY SYSTEM

(75) Inventors: Franz-Peter Barthold, Balingen (DE); Rainer Lesmeister, Reutlingen (DE)

(73) Assignee: JOTEC GmbH, Hechingen (DE)

( * ) Notice: Subject to any disclaimer, the term of this patent is extended or adjusted under 35 U.S.C. 154(b) by 954 days.

(21) Appl. No.: 11/937,824

(22) Filed: Nov. 9, 2007

(65) Prior Publication Data

US 2009/0099637 A1     Apr. 16, 2009

(30) Foreign Application Priority Data

Nov. 9, 2006  (DE) .......................... 10 2006 053 748

(51) Int. Cl.
*A61F 2/06* (2013.01)

(52) U.S. Cl.
USPC ................... 623/1.11; 623/1.12; 623/1.23

(58) Field of Classification Search
USPC ........................................ 623/1.11, 1.12, 1.23
See application file for complete search history.

(56) References Cited

U.S. PATENT DOCUMENTS

| | | | |
|---|---|---|---|
| 2004/0148008 A1* | 7/2004 | Goodson et al. | 623/1.12 |
| 2005/0049674 A1* | 3/2005 | Berra et al. | 623/1.13 |
| 2008/0071343 A1* | 3/2008 | Mayberry et al. | 623/1.11 |

FOREIGN PATENT DOCUMENTS

| | | |
|---|---|---|
| EP | 1 369 098 | 12/2003 |
| EP | 1369098 A1 * | 12/2003 |
| EP | 1 440 673 | 7/2004 |
| WO | WO-2005/023149 | 3/2005 |

OTHER PUBLICATIONS

European Search Report for EP 07079506, mailed Feb. 19, 2008, 2 pages.

* cited by examiner

*Primary Examiner* — Victor Nguyen
*Assistant Examiner* — Kevin Everage
(74) *Attorney, Agent, or Firm* — Morrison & Foerster LLP

(57) ABSTRACT

The present invention relates to a delivery system for a self-expanding stent with a hollow cylindrical body and a proximal and a distal end. At least the proximal end thereof has projecting loops pointing alternately in the proximal and distal direction, the loops having a shoulder and straight sections. In addition, there is an outer tube which passes through the stent and an inner tube which passes through the outer tube, the inner tube and the outer tube being designed to move axially with respect to one another. In addition, it is fitted with a locking system for the projecting loops at the proximal end of the stent for introduction of the stent into the body vessel, the locking system having a cap element with pin elements fixed to it which point axially in the proximal direction of the delivery system and a first engagement unit for the pin elements which is positioned proximal with respect to the cap element in the delivery system.

12 Claims, 4 Drawing Sheets

STENT DELIVERY SYSTEM

CROSS-REFERENCES TO RELATED APPLICATIONS

This application claims priority from German patent application DE 10 2006 053 748.3 filed on Nov. 9, 2006. The content of the above patent application is incorporated by reference herein in its entirety.

BACKGROUND OF THE INVENTION

The present invention concerns a delivery system for the introduction and release of a self-expanding stent in a body vessel, the self-expanding stent having a hollow cylindrical body and a proximal and a distal end, in which at least the proximal end has projecting loops pointing alternately in the proximal and distal direction, the loops having shoulders and straight sections.

Vascular stents, also called endovascular stents, are introduced into vessels to maintain patency, and are described in detail in the prior art. For example, vascular stent grafts can be introduced into damaged or occluded vessels to replace the vessel walls at the damaged or occluded points. A stent graft for this purpose has both a framework, which is usually made of wire, and a coating of biocompatible material.

Stents known from the prior art are, for example, used in vessels whose walls are thinned or thickened by disease or injury and which require support for that reason.

Many stents represent self-expanding stent systems which are introduced into the vessel in a compressed state and which are allowed to expand by removal of compressive structures. Such self-expanding stents must, therefore, contain an elastic material which can expand outwards, i.e., radially, as soon as force exerted to compress the material, e.g., a sleeve, is removed. Preferably, Nitinol is used, which can also have shape-memory properties, for this purpose. The framework of the stent is made of this material and preferably has a tubular structure, which usually has a slightly larger diameter than the vessel into which it is to be implanted.

The introduction and implantation of a stent or stent graft is generally carried out using a delivery system which has two tubular structures, namely an inner piston and an outer sleeve which can be moved axially with respect to one another. The stent is placed inside the distal end of the outer sleeve in a compressed state and is introduced into the vessel in this state. After placing the stent in the desired position, the piston is usually kept stationary, whereas the sleeve of the delivery system is drawn back, releasing the stent. Because of stop contact with the piston, the stent cannot move in the direction of the withdrawn sleeve when it is removed. The stent unfolds because of its self-expanding properties and presses against the vessel walls.

In the prior art, the end of the stent placed closer to the heart is usually designated as the proximal end whereas the end of the stent further away from the heart is designated as the distal end. In contrast, the designation of the ends of the delivery system as distal and proximal is such that the end closer to the operator is designated proximal and the other end further away from the operator is designated distal.

The proximal end of the stent or stent graft is typically designed such that the stent is mainly fixed to the vessel wall by this end. This is intended to prevent movement of the stent after its introduction in the vessel. The ends of the stent have spring components which form meandering encircling projecting loops or pointed arches which expand radially after their release and act as components for fixation to the vessel wall. In the expanded state, the proximal end with these fixation components or projecting loops/pointed arches usually has a larger diameter than the vessel into which the stent is introduced, precisely so that the projecting loops/pointed arches on the proximal end of the stent at least come into firm contact with the vessel walls and can become anchored there. For this reason, these projecting loops/pointed arches on the proximal end of the stent must be squeezed or compressed to introduce the stent and must be secured in the delivery system in such a way that they can be released.

In the case of many stents known from the prior art, both the remainder and the proximal end of the stent are compressed by the sleeve which holds the stent in the compressed state during introduction into the vessel.

The prior art also describes delivery systems which permit separate release of the proximal end of the stent from the rest of the stent.

A frequent problem in this regard is that it is necessary when introducing the system and the stent to withdraw the system slightly before expansion, as the stent or system was pushed too far forwards in the vessel. During this withdrawal, many stents and delivery systems in the prior art have the disadvantage that the projecting loops in the proximal end of the stent become caught in the vessel wall.

RELATED PRIOR ART

To solve this problem, the prior art describes, for example, the delivery system in EP 1 369 098 A1, which has a cap in which the proximal, spring ends of the stent are introduced and held in place, and from which they are then released by a mechanism in the cap or by removal of the cap.

From WO 2005/023149, a delivery system for a stent or stent graft is known in which the springs of the stent are held together by a capture system for the tips of the stent springs. This capture system has an appropriate number of fixed elongated projections onto which the springs are threaded. The projections are fixed to an outer tube or catheter which passes through the lumen of the stent. By pulling back the tube, i.e., by pulling the tube together with the projections which are fixed to it in the direction of the operator, the springs at the proximal end of the stent, which are threaded round the projections, are released.

The disadvantage of the systems known from the prior art is that there is a danger—e.g., if the springs and the system which holds them in place get caught or if the capture system does not fully detach when it is withdrawn—that it may not be possible to release the proximal end of the stent. In addition, the system known from WO 2005/023149 has the disadvantage that twisting the outer catheter involves the risk of twisting the stent as well.

An object of the present invention is, therefore, to make available a delivery system which overcomes the known disadvantages in the prior art.

SUMMARY OF THE INVENTION

According to the invention, this object is solved by a modified embodiment of the delivery system described at the outset, which has an outer tube which passes through the stent and an inner tube which passes through the outer tube, the inner tube and the outer tube being designed to move axially with respect to one another, and which has a locking system for the projecting loops/pointed arches at the proximal end of the stent for introduction of the stent into the body vessel, the locking system having a cap element with pin elements fixed to it which point axially in the proximal direction of the delivery system and a first engagement unit for the pin elements which is positioned proximal with respect to the cap element in the delivery system.

This object of the invention is fully solved in this way.

With the delivery system according to the invention, and in particular with the locking system contained therein with a cap element and an engagement unit for the proximal end of the stent, it is now possible to release the projecting loops/pointed arches without a danger of them jamming in the release system. In addition, there is another advantage in that all components, including the projecting loops, stent and locking system—or fixation system, are prevented from rotating in opposite directions to one another, so that the delivery system can pass on torque. This has the advantage that, if the stent is initially placed inaccurately, it can be rotated along its own axis, to position it correctly in the vessel. The parts of the stent are not twisted with respect to one another in the process, as the locking of the projecting loops at the proximal end of the stent by the pin elements attached to the cap element ensures that it cannot rotate.

The pin elements should preferably be arranged around the circumference of the cap element.

Throughout this application, "tubes" are taken to mean all suitable devices with the properties of a cylindrical or tubular hollow body, for example, a catheter.

Throughout this application, "projecting loops/pointed arches" are taken to mean any mesh structure at the proximal end of a stent which have curved sections at the extreme ends of the stent and sections which are straighter than the curved sections. It is therefore obvious that both stents and stent grafts can be introduced into a body vessel with the delivery system according to the invention.

In an embodiment, the cap element is fixed to the inner tube, and in such a way that movement of the inner tube in the distal direction in relation to the operator can release the projecting loops at the proximal end of the stent from the locking system and allow them to expand.

In the delivery system according to the invention, therefore, the proximal end of the stent intended for introduction into a vessel is fixed over the pin elements of the locking system in the delivery device. Each pin element grips into one projecting loop and is, so to speak, threaded through it. The pin elements pass further into the engagement unit, so that the projecting loops are locked between the cap element and the engagement unit. When the stent is correctly positioned in the vessel the inner tube is moved in the distal direction with respect to the outer tube on which the stent is positioned, that is, away from the operator. Thus, the pins first slide out of the engagement unit and then out of the projecting loops, so that they are freed and expand radially in the direction of the vessel wall. As a result, the proximal end of the stent widens in a collar-like manner and, in its final expanded state, has a diameter which is distinctly larger than the elements of the locking system, so that, in subsequent steps, e.g., after complete release of the stent, the locking system can be drawn back through the stent, i.e., in the direction of the operator, and out of the vessel.

In another embodiment of the delivery system, the first engagement unit for the pin elements pointing in the proximal direction of the delivery system is fixed to the outer tube in such a way that the first engagement unit and the cap element can move axially with respect to one another.

This arrangement has the advantage that no relative movement with respect to the stent occurs during release of the projecting loops. To release the stent, therefore, the inner tube is moved distally, that is away from the operator, with the outer tube remaining in the same position. As a result, the cap element fixed to the inner tube and the pin elements attached to it also move in the distal direction, and the pin elements are first pulled out of the engagement unit connected with the inner tube and then out of the projecting loops, as it were. The remaining part of the stent is unaffected by the release movement of the proximal end of the stent. The guidance provided by the pin elements simultaneously ensures that the proximal end of the stent cannot move with respect to the rest of the stent.

The pin elements should preferably be made of or contain a metal, preferably a metal with a memory effect.

In another embodiment, the first engagement unit has at least one hole for the engagement of the pin elements.

This arrangement has the advantage that the pin elements are easy to engage into the engagement unit. By having pin elements with a certain length limit, it is possible to ensure that the ends of the pin elements are inside the engagement unit. The holes should be parallel to the long axis of the delivery system, and thus also parallel to the direction of the pin elements. The hole can pass all the way through the engagement unit, i.e., from the end of the engagement unit which points towards the cap element to the end which points away from the cap element. It is preferable if the number of holes is the same as the number of pin elements.

In another embodiment, the first engagement unit will have long grooves on its surface axial to the delivery system to accept the straight sections of the projecting loops.

This embodiment has the advantage that the straight sections of the projecting loops at the proximal end of the stent can fit into the grooves, and thus will not project as bulges on the surface of the engagement unit. This ensures reduced friction.

In a further embodiment of the delivery system according to the invention, the first engagement unit has a shape with one first end pointing towards the cap element and a second end pointing away from the cap element, at least the first end of the first engagement unit having a smaller diameter than a middle section between the first and second ends.

This arrangement has the advantage that the middle section of the engagement unit has a shape which curves outwards, as it were, over which the proximal end of the stent is fitted. Because of the smaller diameter of this end, the projecting loops are drawn together again in the next section of the engagement unit which points towards the cap element and locked in place, threaded by the pin elements which pass through them and which are inserted into the engagement unit.

In a further embodiment of the delivery system according to the invention, the locking system also has a second engagement unit positioned axially between the cap element and the engagement unit with holes passing through it to releasably insert the pin elements, the second engagement unit being fixed to the outer tube at an axial distance from the first engagement unit in such a way that the first and second engagement units fixed to the outer tube can move axially with respect to the cap element fixed to the inner tube.

This arrangement has the advantage that correct guiding of the pin elements is guaranteed and the ends of the pin elements are only briefly free, when they are drawn out of the engagement unit, for release of the projecting loops. The second engagement unit thus, in addition to ensuring correct guidance of the pins during release, ensures that the ends of the pin elements are not free, and thus cannot get stuck or caught in the vessel or other parts of the delivery system either.

The second engagement unit can, e.g., have long depressions on its surface in the axial direction relative to the delivery system with bulges between them.

This feature has the advantage that the holes through which the pin elements pass can be in the bulges, so that less material is needed for construction and there is less frictional surface area.

According to another embodiment, the number of pin elements corresponds with the number of projecting loops at the proximal end of the stent.

In this way, every projecting loop at the proximal end of the stent has a corresponding pin element threaded through it. Accordingly, each pin element which passes through the second engagement unit can then be inserted into a corresponding hole in the first engagement unit. In general, it is preferable if at least two pin elements are fitted to lock at least two projecting loops in place. It is obvious that the delivery system according to the invention, in particular its locking system, can be adapted to different stents or stent ends, and that, therefore, the number of pin elements will vary depending on the number of projecting loops. The system according to the invention can thus, for example, be adapted for stents with three, four, five, six, or more projecting loops at the proximal end.

In another embodiment, the system also has a conical tip which contains the cap element of the locking system.

This arrangement has the advantage that the tip, with which most stent delivery systems are fitted, can simultaneously be used to contain the cap element. The cap element, with its pin elements pointing in the proximal direction, is thus firmly integrated in the tip and moves together with it when the inner tube is moved.

In another embodiment of the delivery system according to the invention, it also has a retractable sleeve which holds the stent in a compressed state for introduction into a body vessel.

As mentioned above, the locking system can be used for targeted release of the proximal end of the stent. The remaining sections of the stent can then be compressed for introduction of the stent into a body vessel independently from the proximal end of the stent by applying force with a sleeve fitted over the stent, and can be released by drawing back the sleeve. The stent can thus fully expand and anchor itself in the vessel.

In addition, another embodiment will comprise a pusher which, in combination with a removal of the retractable sleeve, can release the distal end of the stent and the part of the stent between the distal end and the proximal end.

With this pusher it is possible to resist the force needed to remove the sleeve from the stent. This means that the stent does not move in the proximal direction with the retractable sleeve, but can remain in the position where its release was originally intended to occur.

According to another embodiment, the delivery system—either all of it or only parts thereof—is constructed of one or more radiopaque materials.

It will be appreciated, that the above-mentioned features, which are discussed in more detail below, can be used not only in the combination respectively cited, but also alone or in other combinations, without departing from the scope of the present invention.

BRIEF DESCRIPTION OF THE DRAWINGS

The invention is described in more detail by the description and the previously omitted figures below. They show.

Figures 1A, 1B:
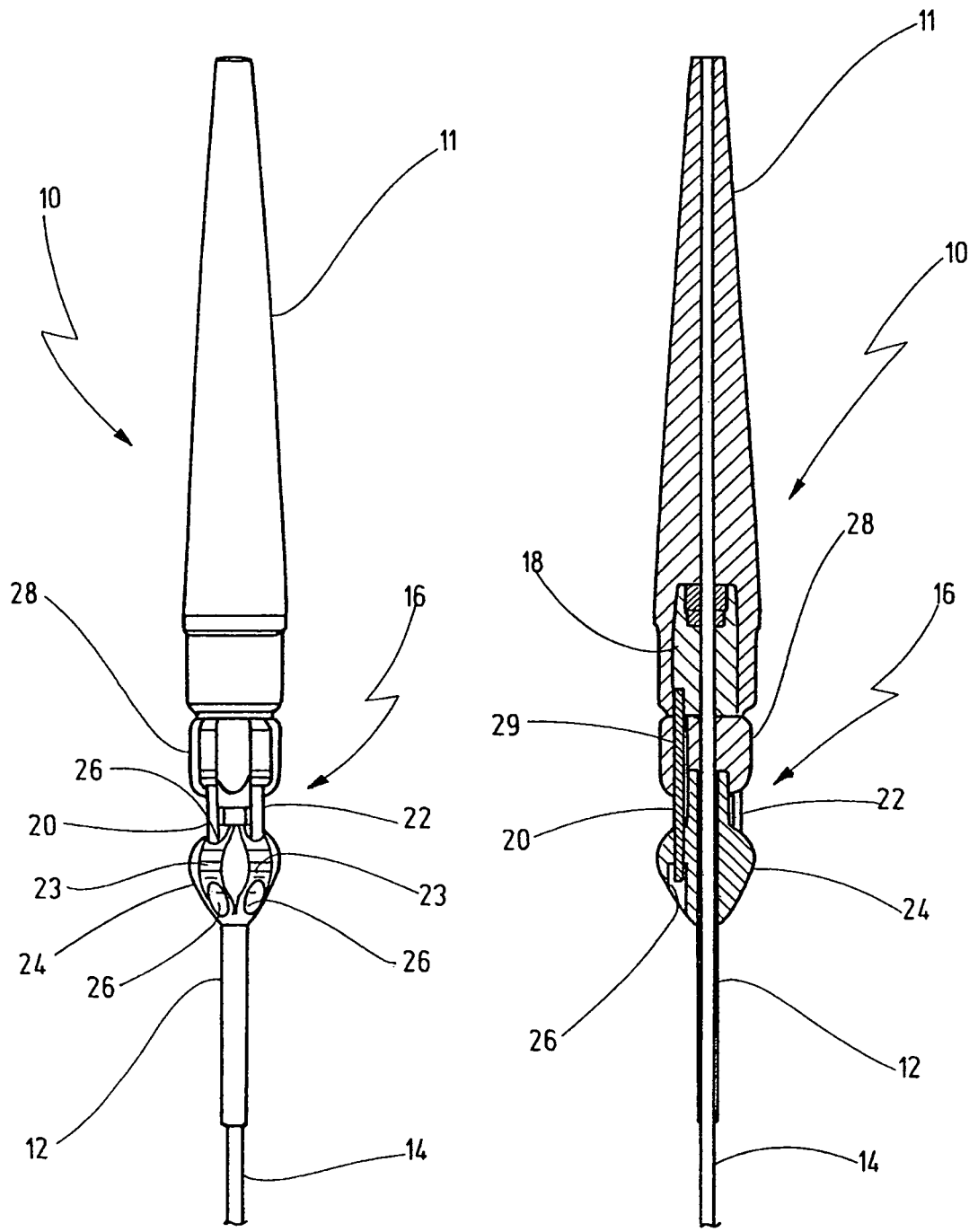
FIG. 1a: A side view of the distal section of an embodiment of the delivery system according to the invention
FIG. 1b: A longitudinal section of the embodiment of the delivery system according to the invention shown in FIG. 1a FIG. 1c: Another view of the embodiment of the delivery system according to the invention shown in FIG. 1a, from the side and front

The delivery system which is fitted with a tip 11 contains an outer tube 12 and an inner tube 14. It also has a locking system, marked overall by 16 in FIGS. 1a, 1b and 1c. The locking system 16 contains a cap element 18 which in turn is fitted with pin elements 20, 22 which are fixed to it. In addition, it has a first engagement unit 24 which has holes 26, into which the pin elements 20, 22 in FIGS. 1a, 1b and 1c fit. The first engagement unit 24 has grooves 27 on its outer surface, with bulges 23 between them.

The cap element 18 is firmly attached to the inner tube 14, the first engagement unit 24 is firmly attached to the outer tube 12. As can be seen from FIG. 1b, the cap element is fixed inside the tip 11 of the delivery system. The tip 11 can be made of a soft material.

In addition, a second engagement unit 28 is provided, positioned between the first engagement unit 24 and the cap element 18. The second engagement unit 28 also has holes 29 through which the pin elements 20, 22 connected in the cap element 18 pass. This second engagement unit 28 is also fixed to the outer tube 12.

Figure 2:
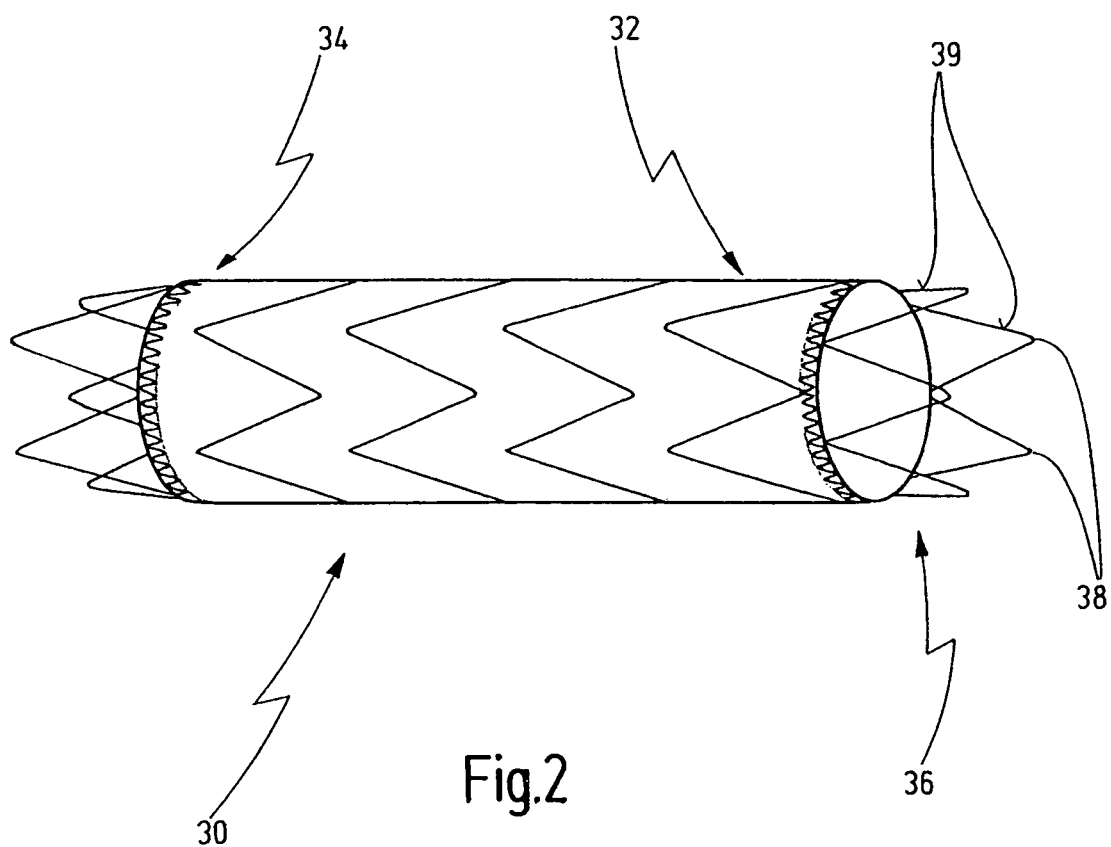
FIG. 2: An example of a stent in its expanded form

FIG. 2 shows an example of a stent 30 with a cylindrical hollow body and a proximal 32 and a distal 34 end. The proximal end of the stent 32 has projecting loops, marked overall by 36 in FIG. 2. These projecting loops 36 have shoulders 38 and straight sections 39.

It is appreciated that the stent or the proximal stent end to be introduced can also have other shapes as projecting loops; what is essential is the mesh-like structure of the end of the stent, which can be gripped and locked in place by the delivery system or locking system according to the invention.

Figure 1C:
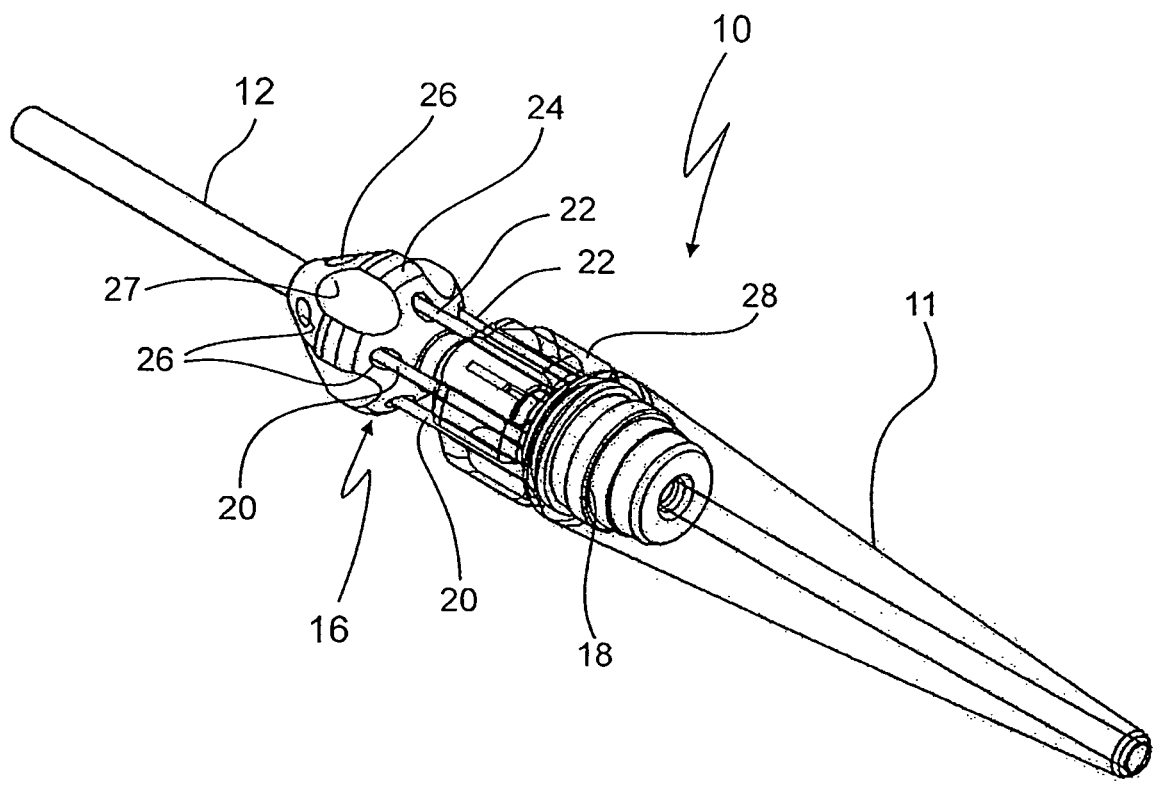
Figure 3:
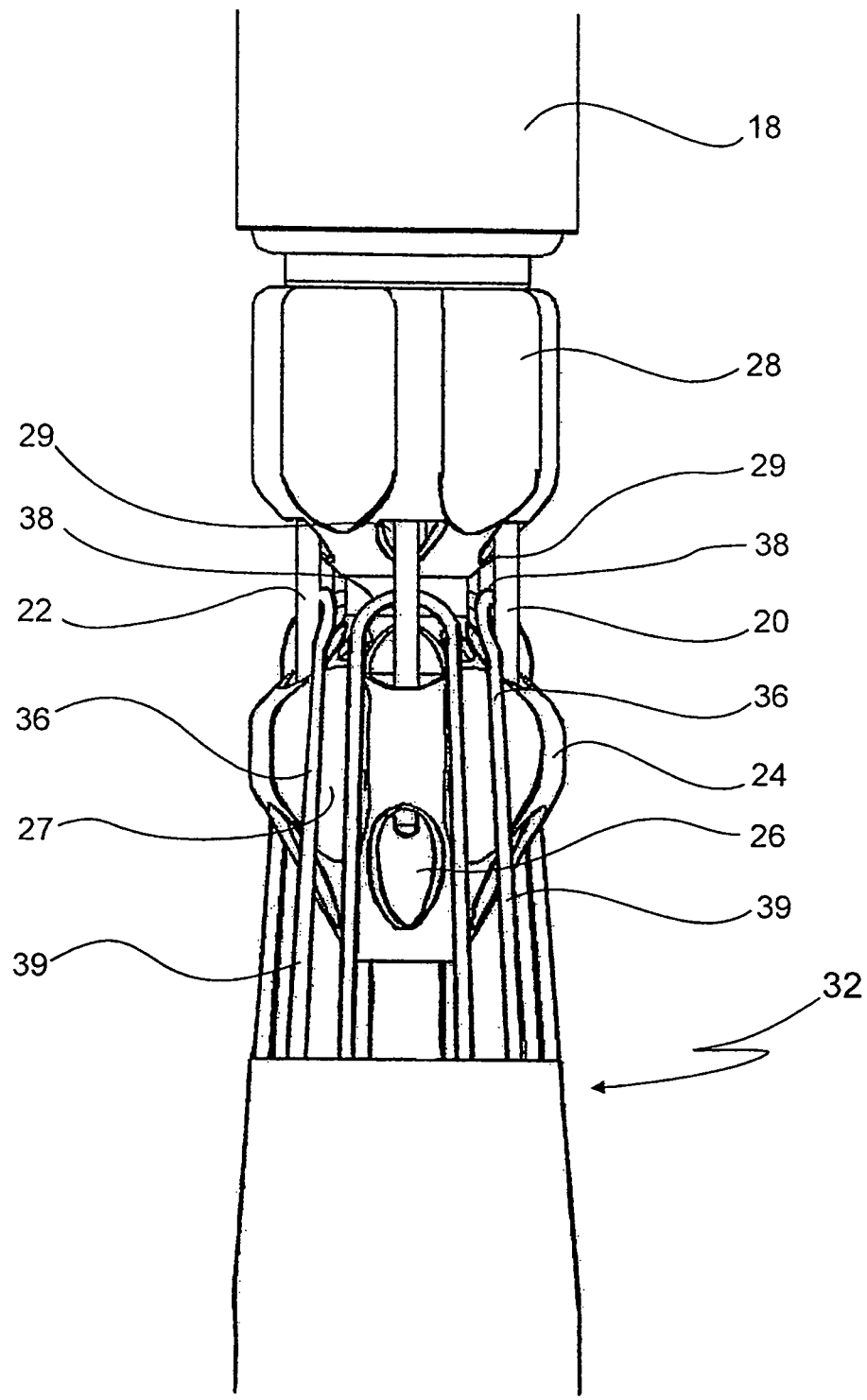
FIG. 3: A side view of the distal section of an embodiment of the delivery system according to the invention fitted with a stent, with the proximal end of the stent being held in place here by the locking system of the embodiment according to the invention for introduction of the stent into a vessel In FIG. 1a, FIG. 1b and FIG. 1c, 10 indicates a delivery system according to the invention as a whole, with FIG. 1a showing a side view of the distal section of this embodiment, FIG. 1b a longitudinal section of the distal section of the embodiment shown in FIG. 1a, and FIG. 1c a view of the embodiment shown in FIGS. 1a and 1b, from the side. In the three figures the same components are indicated by the same reference numbers. For the sake of clarity, the stent and other common features of a stent delivery system have been omitted.

FIG. 3 shows an enlarged section of an embodiment of the delivery system according to the invention, in which the same components as in FIGS. 1a, b, c and 2 have the same reference numbers.

FIG. 3 shows the distal section of a delivery system 10. This has a locking system 16, which includes a cap element 18 and pin elements 20, 22 which are fixed to the cap element. FIG. 3 also shows that the locking system has a first engagement unit 24 with holes 26 into which the pin elements 20, 22 fit. The first engagement unit 24 also has grooves 27 in its outer surface as in FIG. 1. 28 designates a second engagement unit, positioned between the first engagement unit 24 and the cap element 18. As can be seen from FIG. 3, the second engagement unit 28 also has holes 29 through which the pins 20, 22 pass.

Because of the holes 29 the second engagement unit 28 has on its surface alternating bulges which contain the holes 29 and grooves.

FIG. 3 also shows the proximal end of a stent 32 which has projecting loops 36 with shoulders 38 and straight sections 39. With the delivery system loaded, the straight sections 39 of the projecting loops 36 fit in the grooves 27 on the first engagement unit 24.

As shown in FIG. 3, the pin elements 20, 22 which are fixed to the cap element 18 pass through the holes 29 into the second engagement unit 28. In addition, they pass through the projecting loops 36, since the shoulders 38 of which stick out from the first engagement unit 24, because of its shape, so that it is easy for the pin elements 20, 22 to pass through the projecting loops. The pin elements 20, 22 then also pass through the holes 26 in the first engagement unit 24, so that the projecting loops 36 of the stent 30 are locked in place.

It is appreciated that the shape of the first engagement unit 24 can also be different from that shown in the figure, but it is important that the shape of the first engagement unit and the shape of the proximal end of the stent to be implanted, or the loops of this stent, fit together. It is also appreciated that the number of pin elements 20, 22 should match the number of loops or projecting loops on a stent which is to be locked in place with the locking system for the introduction of the stent into a vessel.

Next, it is described how a stent is loaded into the delivery system: to load a stent 30 into the delivery system for the implantation and release of the stent into a body vessel, it is guided over the outer tube 12 and the proximal end of the stent 32 is placed over the first engagement unit 24. In the process, the straight sections 39 of the projecting loops 36 are arranged in the groove 27 on the surface of the first engagement unit 24. The central section of the first engagement unit 24 has a larger diameter than its two end sections, and thus has a spherical or bulbous shape. The pin elements 20, 22 are not located in the holes 26 of the first engagement unit 24 in this state. To lock the proximal end of the stent 32 in place the pin elements 20, 22 are passed through the second engagement unit 28 by moving the inner tube 14, and thus the cap element 18 firmly attached to it. The ends of the pin elements 20, 22 then grip in the projecting loops 36 and thread through them, as it were. With the projecting loops threaded onto them, the pin elements 20, 22 are advanced further into the holes 26 in the first engagement unit 24 and thus lock the proximal end of the stent 32 in place.

In the process, the straight sections 39 of the projecting loops 36 come to lie in the grooves 27 which are intended to accept the straight sections 39 on the surface of the first engagement unit 24. The fact that the straight sections 39 fit "smoothly" in the grooves 27 avoids these sections projecting as bulges on the surface of the first engagement unit 24 and causing unnecessary friction.

The remaining sections of the stent are held in a compressed state by a retractable sleeve (not shown). The stent is introduced into a body vessel in this compressed and locked state. To do this, a guide wire is usually also fitted through the inner tube 14 and the tip 11. Appropriate markers, for example X-ray markers, can be used to monitor exact placement of the stent.

When the delivery system and the compressed stent contained therein reach the point at which the stent is to be placed, the inner tube 14 is first operated and moved forwards, in the distal direction (away from the operator). As the inner tube 14 moves in the distal direction, the cap element 18 which is fixed to it also moves in the distal direction. Because the pin elements 20, 22 are fixed to the cap element 18, they are also indirectly moved in the distal direction by moving the inner tube 14. As a result, they emerge from the holes 26 in the first engagement unit 24 and release the projecting loops 36 at the proximal end of the stent 32 through which they were threaded. These can then expand, and attach themselves to the vessel wall. The remaining sections of the stent can be released from the delivery system 10, for example by removing one of these retractable sleeves that holds them in a compressed state. By passive movement of the pin elements 20, 22 they are guided through the holes 29 in the second engagement unit 28 and remain with their ends held therein. This avoids the exposure of sharp ends, which is an advantage, particularly when withdrawing the inner tube 14 through the stent 30 and through the delivery system 10 in the direction of the operator, because this means that there is no danger of the free sharp ends catching in the surrounding tissue.

The stent 30 which is normally located on the outer tube 12 is protected from relative movements by the delivery system according to the invention upon release of the proximal end 32, as only the inner tube 14 moves, and the outer tube 12 remains stationary. In addition, the locking system 16 prevents all parts rotating, so that torques can be transferred to the system.

The invention claimed is:

1. A delivery system for the introduction of a self-expanding stent into a body vessel, the delivery system comprising:
   a self-expanding stent with a hollow cylindrical body and a proximal and a distal end, in which at least the proximal end has projecting loops pointing alternately in the proximal and distal direction, the loops having a shoulder and straight sections,
   an outer tube which passes through the stent and an inner tube which passes through the outer tube, the inner tube and the outer tube being designed to move axially with respect to one another, and
   a locking system for the projecting loops at the proximal end of the stent for introduction of the stent into the body vessel, the locking system having a cap element with pins fixed to it which point axially away from the cap in the proximal direction of the delivery system and a first engagement unit for the pins which is positioned proximal with respect to the cap element in the delivery system,
   wherein the cap element is fixed to the inner tube in such a way that movement of the inner tube in the distal direction can release the projecting loops at the proximal end of the stent from the locking system and allow them to expand, wherein the first engagement unit for the pins pointing in the proximal direction of the delivery system is fixed to the outer tube in such a way that the first engagement unit and the cap element can move axially with respect to one another.

2. A delivery system according to claim 1, wherein in the locking system, the first engagement unit has at least one hole for the releasable engagement of the pins.

3. The delivery system according to claim 1, wherein in the locking system, the first engagement unit has long grooves on its surface axial to the delivery system to accept the straight sections of the projecting loops.

4. The delivery system according to claim 1, wherein in the locking system, the first engagement unit has a shape designed to fit the hollow cylindrical body of the stent with one first end pointing towards the cap element and a second end pointing away from the cap element, at least the first end of the first engagement unit having a smaller diameter than a middle section between the first and second ends.

5. The delivery system according to claim 1, wherein the locking system also has a second engagement unit positioned axially between the cap element and the first engagement unit with holes passing through it to guide the pins; the second engagement unit of which is fixed to the outer tube at an axial distance from the first engagement unit in such a way that the first and second engagement units fixed to the outer tube can move axially with respect to the cap element fixed to the inner tube.

6. The delivery system according to claim 5, wherein the second engagement unit has long depressions on its surface in the axial direction relative to the delivery system with bulges between.

7. The delivery system according to claim 1, wherein the number of pins corresponds with the number of projecting loops at the proximal end of the stent.

8. The delivery system according to claim 1, wherein it is fitted with at least two pins.

9. The delivery system according to claim 1, wherein it also has a conical tip which contains the cap element of the locking system.

10. The delivery system according to claim 1, wherein it also has a retractable sleeve which holds the stent in a compressed state for introduction into a body vessel.

11. The delivery system according to claim 1, wherein it also has a pusher which, in combination with a removal of the retractable sleeve, can release the distal end of the stent and the part of the stent between the distal end and the proximal end.

12. The delivery system according to claim 1, wherein the delivery system as a whole or parts thereof is/are constructed of one or more radiopaque materials.

* * * * *